Figure 1:
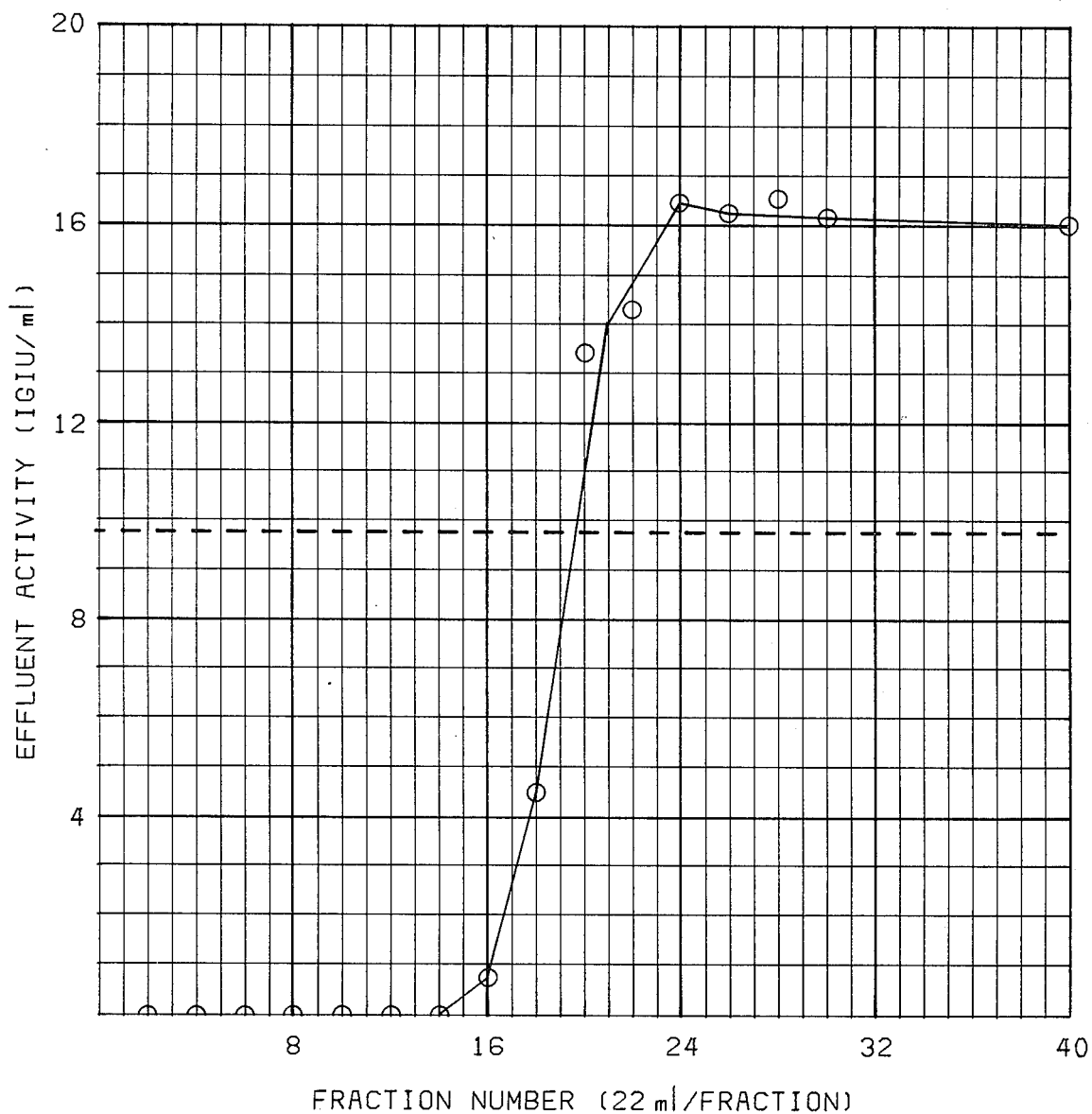

United States Patent [19]

Johnson et al.

[11] 4,347,322

[45] Aug. 31, 1982

[54] CHROMATOGRAPHIC PROCESS FOR ENZYME PURIFICATION

[75] Inventors: Richard A. Johnson; Norman E. Lloyd, both of Clinton, Iowa

[73] Assignee: Nabisco Brands, Inc., New York, N.Y.

[21] Appl. No.: 224,590

[22] Filed: Jan. 12, 1981

[51] Int. Cl.³ .................. C12N 11/12; C12N 9/26; C12N 9/92

[52] U.S. Cl. .................................. 435/179; 435/180; 435/201; 435/205; 435/234; 435/815

[58] Field of Search ............... 435/94, 234, 815, 174, 435/179, 178, 177, 180, 201, 205

[56] References Cited

U.S. PATENT DOCUMENTS

| | | | |
|---|---|---|---|
| 3,708,397 | 1/1973 | Sipos | 435/179 |
| 3,788,945 | 1/1974 | Thompson et al. | 435/94 |
| 3,909,354 | 9/1975 | Thompson et al. | 435/94 |
| 3,960,663 | 6/1976 | Tamura et al. | 195/31 |
| 4,012,571 | 3/1977 | Dean et al. | 526/50 |
| 4,106,992 | 8/1978 | Vairel et al. | 195/66 |
| 4,113,568 | 9/1978 | Fujita et al. | 195/68 |
| 4,263,400 | 4/1981 | Ushiro | 435/815 X |

FOREIGN PATENT DOCUMENTS 2022096  4/1981  United Kingdom .............. 435/177

OTHER PUBLICATIONS

"Methods in Enzymology", vol. XXII, Enzyme Purification and Related Techniques, pp. 273-286, 345-378, 518-524, Academic Press, New York, 1971.

"Encyclopedia of Chemical Technology", Kirk-Othmer, Second Edition, vol. 5, Chromatography, pp. 413-429, 442-449, John Wiley & Sons, New York 1964.

*Primary Examiner*—David M. Naff
*Attorney, Agent, or Firm*—Richard Kornutik; Robert A. Conzett; Henry S. Wyzan

[57] ABSTRACT

Enzyme purification is carried out by contacting an impure liquid enzyme preparation containing enzyme and soluble impurities with an ion exchange material in a column to adsorb both the enzyme and impurities by the ion exchange material, adding an additional amount of the impure liquid enzyme preparation whereby the soluble impurities therein are preferentially adsorbed by the ion exchange material and the adsorbed enzyme is displaced from the ion exchange material to produce a purified liquid enzyme preparation containing higher enzyme activity than before purification. The purified enzyme is more highly adsorbed by ion exchange material when immobilizing the enzyme.

11 Claims, 3 Drawing Figures

ISOMERASE REFINING WITH A FIXED-BED OF DEAE-CELLULOSE

ISOMERASE REFINING WITH A FIXED-BED OF DEAE-CELLULOSE

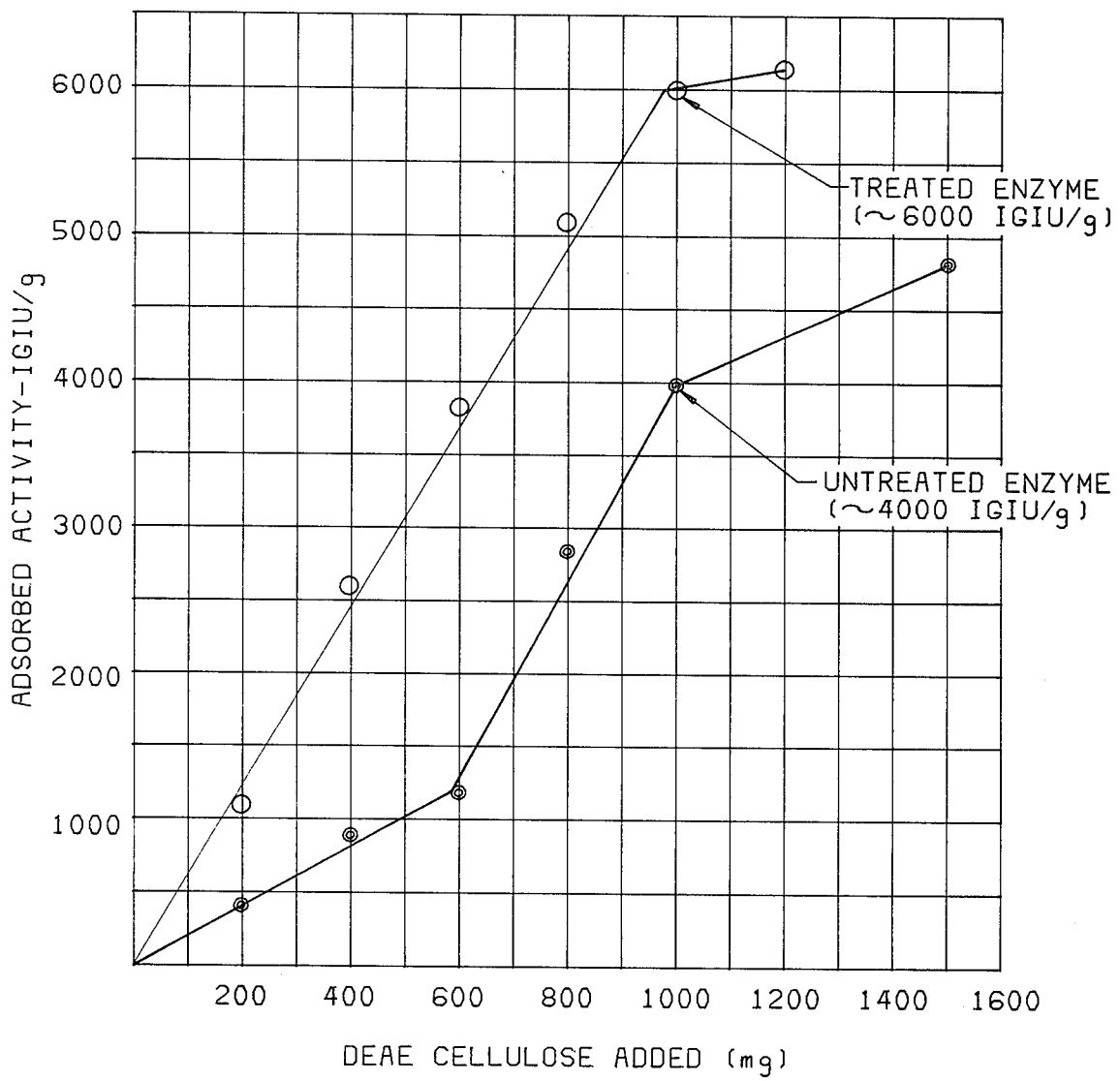

CHROMATOGRAPHIC PROCESS FOR ENZYME PURIFICATION

BACKGROUND

1. Field of the Invention

This invention relates to a process for the purification of enzyme preparations that are highly adsorbed by ion exchange materials. More specifically the invention relates to a process for the purification of enzyme preparations by a chromatographic separation.

2. Description of the Prior Art

Many industrial enzymes of biological origin are utilized in commercial food processes. Enzymes of the amylase type are produced in larger quantities and their value exceeds all the other enzyme preparations produced in the U.S. For example, alpha amylase, beta amylase, and glucoamylase enzymes are widely used in processes to convert starch to glucose, and in the brewing, distilling and baking industries. Glucose isomerase is used to convert glucose to fructose. Invertase is used in the manufacture of liquid and soft centered candies, and for the conversion of sucrose to invert sugar. The invert sugar is used in production of confectionary, cordials, ice cream, and soft drinks. Lactase is used in the manufacture of ice cream and in whey to produce fermentable sugars.

Pectic and protease enzymes are also utilized commercially. Pectic enzymes are used in production of fruit juices and fruit juice products, wines, fermentation of coffee and cocoa beans, and in the rehydration of dehydrated foods. Proteases are used in cheese making, meat tenderizing, bread baking, for haze elimination from beer and other beverages, and in the preparation of digestive aids.

Enzyme preparations are produced by the cultivation of selected strains of microorganisms and are predominantly used in the soluble form. However, in addition to the desirable enzyme, the microorganisms also produce a wide variety of biochemical compounds required for growth and productivity. As a result, soluble enzyme preparations, whether obtained from the extracellular medium or extracted from the microbial cells, usually contain many undesirable impurities. The insoluble impurities can be easily separated by well known methods, such as by filtration or centrifugation. However, the soluble impurities are difficult and expensive to remove because they often have chemical or physical properties similar to the desired product. The enzyme cost is the major factor in determining its commercial acceptability. To minimize enzyme cost, industrial enzyme preparations are purified only to the extent necessary for the desired efficacy in the intended use. As a result, enzymes for industrial use are usually not treated to remove soluble impurities.

One of the major technological advancements in recent years has been the development of processes to produce immobilized (insoluble) enzymes. The immobilized enzymes are particularly adaptable to continuous processes which are more economical than batch processes. For example, immobilized glucose isomerase is utilized in continuous processes to isomerize glucose to fructose in the commercial production of high fructose corn syrup. The production of other immobilized enzymes, such as glucoamylase, invertase, and lactase have also been reported but have not found widespread commercial use.

Glucose isomerase is an intracellular enzyme produced by submerged aerobic fermentation of a selected microorganism. For example, microorganisms of the genera Actinoplanes, Arthrobacter, Lactobacillus and Streptomyces produce intracellular glucose isomerase. Glucose isomerase may be immobilized in the presence of the microbial cells, for example, by a chemical treatment, or the enzyme may be extracted from the cells and separated as a soluble enzyme prior to immobilization on an inert carrier. Both procedures are utilized to produce immobilized enzyme used in the production of high fructose corn syrup.

A procedure for immobilization of glucose isomerase within the microbial cells by a heat treatment is disclosed in U.S. Pat. No. 3,753,858—Takasaki et al. U.S. Pat. No. 3,779,869—Zienty and U.S. Pat. No. 3,980,521—Amotz et al., disclose the immobilization of glucose isomerase with the microbial cells by treatment with gluteraldehyde. U.S. Pat. No. 3,821,086—Lee et al. and U.S. Pat. No. 3,935,069—Long, disclose immobilized glucose isomerase produced by a flocculation of the microbial cells.

Processes for immobilization of a cell-free, soluble glucose isomerase of inert carriers are disclosed in a number of U.S. patents. U.S. Pat. No. 3,708,397—Sipos, U.S. Pat. Nos. 3,788,943 and 3,909,354 both to Thompson et al., and U.S. Pat. Nos. 3,960,663—Tamura et al., disclose methods for immobilizing a soluble cell-free glucose isomerase on an anion exchange cellulose or a synthetic anion exchange resin. U.S. Pat. Nos. 3,850,751 and 3,868,304 both to Messing disclose processes for the immobilization of soluble, cell-free glucose isomerase on a porous ceramic body and a porous alumina body, respectively. U.S. Pat. No. 3,715,277—Dinelli discloses a method for the immobilization of soluble, cell-free glucose isomerase by entrapment in a polymeric fiber.

Glucose isomerase is produced primarily intracellularly and thus the major portion of the glucose isomerase is found within and/or on the cell walls of the microorganisms. Therefore, it is necessary to extract the enzyme from the cells to produce the soluble enzyme. The extraction process, which makes use of a cationic surfactant or other agent, results in at least partial disruption of the cell envelope allowing diffusion of the enzyme and other cellular materials into the extraction medium. After extraction and removal of the insoluble debris, te enzyme is immobilized directly on an insoluble carrier. Typically, the enzyme is adsorbed on an anion exchange matrix such as DEAE-cellulose or a granular ion exchange resin.

The amount of enzyme activity adsorbed on an ion exchange material is not dependent on the concentration of enzyme in enzyme extract, so long as the amount of total activity supplied is sufficient to satisfy the total capacity of the adsorbent. However, the amount of enzyme activity adsorbed is a function of the purity or quality of the soluble enzyme extract. That is, increasing the enzyme purity will result in an increase in the enzyme activity per gram of adsorbent. This is because the soluble impurities may interfere with the enzyme adsorption, or may compete with the enzyme for adsorption on the available ion exchange sites of the insoluble matrix. As a result, ion exchange sites occupied by impurities will not be available for binding of active enzyme. The impurities which compete for the ion exchange sites are believed to be charged biological oligomers or polymers, e.g., nucleic acids, proteins, etc. Removal of those substances which compete with the enzyme for adsorption sites can result in improved adsorption of the enzyme and the resulting immobilized enzyme will have a substantially higher activity per gram. Higher activity is of particular importance when the cost of the matrix is high. Therefore, an economical process to remove the soluble impurities would be desirable.

Methods for removal or separation of undesirable materials for biological extracts are well known. A current summary of these methods can be found in Volume XXII of "Methods in Enzymology" pp. 273–287 and pp. 476–556 (ed. W. E. Jakoby, Academic Press, N.Y., N.Y.). Various separation methods for enzyme purification, such as separation based on solubility, separation based on specific affinity and chromatographic separations are described.

Column chromatography is a widely used laboratory technique for enzyme purification. In this method, the enzyme is adsorbed on an ion exchange material, such as DEAE-cellulose or CM-cellulose, while the impurities remain in the effluent from the column. The enzyme is then eluted from the adsorbent by the addition of a solution containing an agent, such as a salt, to affect a change in ionic strength or pH. On a laboratory scale, this type of separation produces a highly purified product with good recovery of the total enzyme activity. However, the agent used to elute the enzyme from the ion exchange adsorbent interferes with the subsequent enzyme immobilization. Therefore, the eluting agent must be removed before the purified enzyme can be efficiently immobilized on an insoluble carrier. The added cost of this separation step is relatively unimportant in a laboratory process where the goal is to produce a highly purified enzyme. However, cost is important in commercial use where the goal is to produce an enzyme at a minimum cost which will produce economically acceptable results. The need for careful control of operating conditions is also a drawback. Thus, commercial use of a chromatographic separation or refining process is limited by the overall cost, which may outweigh the benefits.

Numerous patents also describe various methods for purification of enzymes. U.S. Pat. No. 3,769,168 to Masuda describes the purification of beta amylase by adsorption, washing and eluting the enzyme with an ionic solution. U.S. Pat. No. 3,912,595 to Philipp et al. describes the purification of a hydrolytic enzyme solution by reversibly complexing the enzyme on a granular support material in a column, after which the enzyme is recovered by elution with a buffer. U.S. Pat. No. 3,972,777 to Yamada et al. describes a method to refine α-galactosidase by selective adsorption on an acidic cation exchange resin and then eluting the α-galactosidase from the resin with a buffer. All of these methods encompass contacting an impure enzyme solution with a matrix which will adsorb or bond the enzyme, and then eluting the purified enzyme from the matrix by addition of an ionic solution. The cost of elution and recovery of the purified enzyme has been a deterrent to achieving commercial acceptability.

In U.S. Pat. No. 4,106,992 to Vairel et al., crude urokinase is subjected to exclusion chromatography utilizing a DEAE-cellulose resin. The described process is principally directed to removing pyrogenic substances from urokinase. The disadvantages are that it is a cumbersome process and requires conductivity and pH conditions which are critical to achieve the desired results. Salts, such as ammonium sulfate, are utilized to achieve the required conductivity.

U.S. Pat. No. 4,055,469 to Snoke et al. describes the removal of nucleic acids and unwanted proteins from microbial extracts by precipitation.

U.S. Pat. Nos. 3,788,945 and 3,909,354 both to Thompson et al. describes a batch method for purification of a glucose isomerase solution by contacting it with DEAE-cellulose for about 30 minutes, after which the DEAE-cellulose was removed by filtration, the filter cake washed with water and the washings were collected with the enzyme containing filtrate. This process results in dilution of the enzyme preparation. The amount of DEAE-cellulose used in the batch process of Thompson is critical. If an insufficient amount of DEAE-cellulose is used, the maximum purification of the enzyme will not be achieved. If too much DEAE-cellulose is used, some enzyme will be adsorbed and retained on the absorbent resulting in a loss of activity in the purified enzyme.

A description of chromatographic methods contained in the "Encyclopedia of Chemical Technology", Volume 5, pp. 418–420 (Kirk Othmer, 2nd Ed.; Wiley-Interscience, N.Y., N.Y.) includes a method referred to as "Frontal Analysis". The "Frontal Analysis" technique is generally similar to the process of our invention. However, the novelty of our invention is the discovery that ionic biological impurities in an enzyme solution can be used to displace enzyme from an adsorbent using a frontal analysis process.

Throughout this specification and claims, "activity" is defined as units of activity per ml when reference is made to an enzyme solution. "Activity" is defined as units per gram, d. b. when reference is made to an immobilized or dry enzyme preparation.

OBJECTS OF THE INVENTION

It is the object of the present invention to provide a chromatographic method for purifying liquid enzyme preparations wherein soluble ionic impurities are preferentially adsorbed on an ion exchange matrix.

It is the further object of the present invention to provide a chromatographic method for purifying liquid enzyme preparations wherein strongly adsorbed soluble impurities are preferentially adsorbed on an ion exchange matrix and the purified liquid enzyme preparation contains a higher activity than the activity of the enzyme preparation before purification.

It is the still further object of the present invention to provide a purified liquid enzyme preparation that is adsorbed and immobilized by ion exchange materials to produce immobilized enzymes containing increased activity.

These and other objects of the invention will be apparent from the present specification and claims.

SUMMARY OF THE INVENTION

This invention relates to a process for producing a purified enzyme preparation by removing strongly adsorbed soluble impurities from an impure aqueous enzyme preparation by utilization of a chromatographic separation. The chromatographic process comprises contacting an impure liquid enzyme preparation containing strongly adsorbed soluble impurities with an ion exchange material. The strongly adsorbed soluble impurites in the enzyme preparation are preferentially adsorbed by the ion exchange material. A purified liquid enzyme preparation is produced that contains an activity substantially greater than the activity of the impure enzyme preparation. The purified enzyme is also more highly adsorbed by ion exchange material.

This invention also encompasses a high activity immobilized enzyme and process for producing the same by utilization of the purified soluble enzyme preparation.

UTILITY

Soluble enzyme preparations purified by the process of the present invention and adsorbed on ion exchange materials produce an immobilized enzyme with increased activity. When utilized in continuous enzyme catalyzed processes, higher production rates and reduced costs are obtained.

DESCRIPTION OF THE INVENTION

In the process of our invention, an ion exchange material known to adsorb enzymes is utilized to purify an enzyme solution containing soluble ionic biological impurities, with essentially no loss in soluble activity. Furthermore, the purified enzyme solution is more concentrated and substantially devoid of substances which will be preferentially adsorbed or will displace adsorbed enzyme.

Our process comprises passing an impure enzyme solution through a vessel containing an ion exchange material. Initially the enzyme and, presumably, the ionic impurities are adsorbed until the capacity of the adsorbent is satisfied. During this period the effluent from the vessel contains essentially no enzyme activity. When the capacity of the adsorbent is reached and additional enzyme is supplied to the vessel, the effluent contains enzyme activity at a higher concentration than is contained in the vessel influent. This indicates that some enzyme is being desorbed from the adsorbent. We believe that as additional enzyme solution is supplied to the vessel adsorbed enzyme is being displaced by impurities which are more strongly adsorbed. This process continues until all of the adsorbed enzyme is displaced. At this time, the total soluble enzyme activity in the influent is equal to the total soluble enzyme activity in the effluent, with the enzyme activity in the effluent being more concentrated. The purified enzyme is more highly adsorbed by an ion exchange material which results in an immobilized enzyme with a higher activity per gram.

The process of this invention may be utilized to purify a variety of enzymes such as alpha-amylase, glucoamylase, lactase, invertase, protease and the like. The preferred enzyme preparations are aqueous solutions of alpha-amylase, glucoamylase and glucose isomerase. The most preferred is glucose isomerase.

The ion exchange material chosen for enzyme purification will depend on the soluble impurities to be removed. An anion exchange material is preferred for the removal of negatively charged impurities and a cationic material is preferred for the removal of positively charged impurities.

The preferred ion exchange materials are fibrous anion exchange cellulose or synthetic anion exchange resin. Examples of fibrous anion exchange cellulose are di- and triethylaminoethyl cellulose such as DEAE-cellulose and TEAE-cellulose, and cellulose derivatives of epichlorohydrin, and triethanolamine such as EC-TEOLA-cellulose. The preferred anion exchange resins are of the macroporous type. Examples of macroporous anion exchange resins are Amberlite IRA-93, IRA-938, IRA 900 and IRA 910, all manufactured by Rohm & Haas; Duolite A-6 and Duolite A-7 manufactured by Diamond Alkali Company.

The most preferred anion exchange cellulose is a fibrous DEAE-cellulose. A process for the manufacture of fibrous DEAE-cellulose is described in U.S. Pat. No. 3,823,133 and a method for production of an agglomerated fibrous ion exchange cellulose is described in U.S. Pat. Nos. 4,110,164 and 4,168,250.

The temperature and pH conditions utilized in the purification process should be such that the efficacy of the purified enzyme is not deleteriously affected.

Immobilized glucose isomerase is commercially used to isomerize glucose to fructose in the production of high fructose corn syrups. We have made the surprising discovery that treatment of the soluble glucose isomerase by the process of this invention results in a purified enzyme containing increased activity and substantially no loss in activity. In addition, use of the purified enzyme results in an immobilized enzyme containing substantially increased activity. The higher activity of the immobilized enzyme allows increased production rates with a resultant reduced cost to produce high fructose corn syrup.

Although we do not want to be bound by any theory, it is believed that glucose isomerase preparations heretofore immobilized on ion exchange materials contain substantial amounts of soluble charged oligomers or polymers such as nucleic acids and proteins, among other non-enzyme substances. It is believed these non-enzyme anions compete with the enzyme for adsorption on the ion exchange sites of the insoluble matrix. The removal of these non-enzyme substances by the process of our invention results in improved adsorption of the enzyme and a substantial increase in the activity of the immobilized enzyme.

The preferred process of the invention is to pass the glucose isomerase enzyme solution to be purified through a bed or column of DEAE-cellulose. Both the isomerase enzyme and the strongly adsorbed impurities are adsorbed and retained by the DEAE-cellulose in the column until the DEAE-cellulose is saturated. As additional enzyme solution is introduced into the column, the impurities that are more strongly adsorbed than the enzyme displace the adsorbed enzyme until substantially all of the adsorbed enzyme is eluted and recovered in the column effluent. The DEAE-cellulose can be regenerated by a salt wash to elute the strongly adsorbed material followed by water wash to remove residual salt. The enzyme purified in this manner is more highly adsorbed by DEAE-cellulose and the resulting immobilized enzyme has a substantially higher potency per gram of cellulose.

Our inventive process is unique in that we have discovered that an impurity in an enzyme preparation that is more strongly adsorbed than the enzyme can be used to displace enzyme from an adsorbent to effect both a purification and concentration of the enzyme. The enzyme solution produced contains substantially no impurities which will be more strongly adsorbed than the enzyme.

DESCRIPTION OF TERMS AND ANALYTICAL METHODS

Isomerase Activity—IGIU

IGIU is the abbreviation for International Glucose Isomerase Unit and is that amount of enzyme which will convert 1 micromole of glucose to fructose per minute in a solution initially containing 2 moles of glucose per liter, 0.02 moles of $MgSO_4$ and 0.001 mole of $CoCl_2$ per liter at a pH of 6.84 to 6.85 (0.2 M sodium maleate) measured at ambient temperature, and at a temperature of 60° C. Glucose isomerase determinations were carried out by the method described by N. E. Lloyd et al., *Cereal Chem.*, 49, No. 5, pp. 544–553 (1972).

In order to more clearly describe the nature of the present invention, specific examples will hereinafter be described. The examples are primarily directed to the purification and immobilization of glucose isomerase. However, it should be understood that this is done solely by way of example and is intended neither to delineate the scope of the invention nor limit the ambit of the appended claims.

EXAMPLE I

Preparation of DEAE-Cellulose

A DEAE-cellulose derivative was prepared by the method described in U.S. Pat. No. 3,823,133 and then dewatered by filtration to about 25% d.s. The derivatized cellulose was further treated in the following manner, to remove fines. About 300 grams of the wet cellulose was suspended in 3 liters of deionized water, stirred, and the cellulose allowed to settle. The fines were decanted off. This process was repeated 3 more times, after which the DEAE-cellulose was collected by filtration on a sintered glass funnel and washed with about 1000 ml of deionized water. The washed DEAE-cellulose was dewatered to about 25.1% d.s. and stored in the cold until needed.

Preparation of Clarified Isomerase Extract

Glucose isomerase (D-xylose ketol isomerase, E.C. 5.3.1.5) was produced by submerged aerobic fermentation of *Streptomyces rubiginosus* mircoorganisms. The intracellular enzyme was extracted from the mycelia using a cationic surfactant (BTC-835, Onyx Chemical Co., Jersey City, N.J.) and the insoluble material was removed by filtration. The isomerase extract was concentrated to about 179 IGIU/g by vacuum evaporation and stored in the cold.

About 500 grams of the stored concentrated isomerase extract was diluted to about 3000 ml with deionized water, heated to 50° C. and held 30 minutes to redissolve any possible solids that might have precipitated during storage. The diluted enzyme extract was then filtered through a 2 inch precoat of Hyflo Supercel (Johns Manville Corp.) and then through a 0.45μ Millipore filter to reduce potential microbial contamination. This unpurified, clarified isomerase extract, containing an isomerase activity of 22.76 IGIU/ml was identified as Isomerase I and stored in the cold until needed.

A fixed bed of DEAE-cellulose was prepared by suspending 1 g, d.b. of the above described, stored DEAE-cellulose and about 1 g of Hyflo Supercel filter aid in 200 ml of deionized water. The suspension was poured into a Pharmacia 15–40 chromatographic column, 1.5 cm I.D. (Pharmacia Fine Chemicals, Inc.) fitted at the bottom with a screen to retain the suspended solids. The bed was allowed to settle by gravity. After the water had drained off, the bed of DEAE-cellulose in the column measured 9.8 cm by 1.5 cm.

Glucose isomerase for this example was prepared by diluting 898 ml of Isomerase I to a total volume of 2000 ml and adjusting to pH 6.8. The diluted isomerase contained an activity of 9.8 IGIU per ml. The column and enzyme solution were used at ambient temperature.

Initially, about 30 ml of enzyme solution was placed in the column and allowed to flow by gravity. After about 10 ml had flowed from the column, the effluent showed a light yellow color. At this time, enzyme was pumped into the column at a rate of about 1 ml min$^{-1}$, resulting in the residence time of the enzyme in the bed being about 10 minutes. The effluent from the column was then collected in 22 ml fractions. Aliquots of each fraction were assayed for isomerase activity. The results are shown in Table I and illustrated in FIGS. 1 and 2.

TABLE I

| Fraction No. | Column Effluent | | Total Activity (IGIU/ml) | | Net Activity Adsorbed by DEAE-Cellulose[1,3] |
|---|---|---|---|---|---|
| | Total Vol. (ml) | IGIU/ml In Fraction[2] | Inffluent | Effluent | |
| 2 | 34 | 0 | 333 | 0 | 333 |
| 4 | 78 | 0 | 764 | 0 | 764 |
| 6 | 122 | 0 | 1196 | 0 | 1196 |
| 8 | 166 | 0 | 1627 | 0 | 1627 |
| 10 | 210 | 0 | 2058 | 0 | 2058 |
| 12 | 254 | 0 | 2458 | 0 | 2458 |
| 14 | 298 | 0 | 2920 | 0 | 2920 |
| 16 | 342 | 0.7 | 3352 | 15.4 | 3347 |
| 18 | 386 | 4.55 | 3783 | 165 | 3618 |
| 20 | 430 | 13.3 | 4214 | 658 | 3556 |
| 21 | | | | 963 | |
| 22 | 474 | 14.35 | 4645 | 1279 | 3366 |
| 23 | | | | 1619 | |
| 24 | 518 | 16.45 | 5076 | 1981 | 3095 |
| 25 | | | | 2341 | |
| 26 | 562 | 16.10 | 5508 | 2701 | 2807 |
| 27 | | | | 3061 | |
| 28 | 606 | 16.45 | 5939 | 3423 | 2516 |
| 29 | | | | 3783 | |
| 30 | 650 | 16.45 | 6370 | 4145 | 2225 |
| 40 | 870 | 16.45 | 8526 | 7696 | 830 |
| 43 | 950 | | 9310 | 8890 | 420 |

Figure 2:
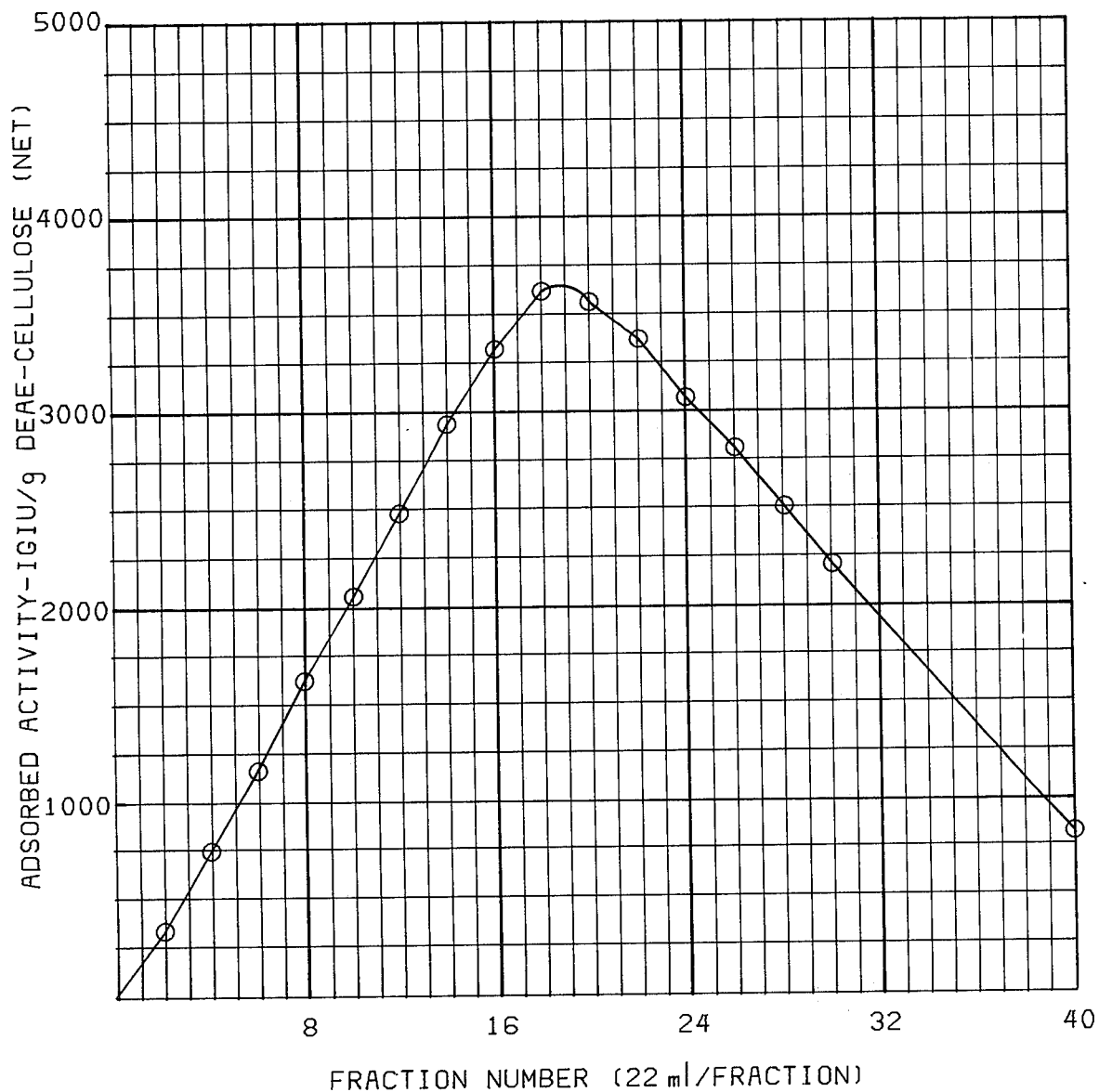

[1]Determined by subtracting the total activity in the effluent from the total activity supplied in the influent.
[2]These data are depicted in FIG. 1.
[3]These data are depicted in FIG. 2.

A total of about 3800 IGIU was applied to the column before a significant amount of enzyme activity appeared in the effluent (Fraction No. 18). After this point the effluent contained an activity (13.5–16.5 IGIU) greater than the 9.8 IGIU contained in the column influent, indicating that something in the influent enzyme was displacing adsorbed isomerase from the DEAE-cellulose bed. A total of 950 ml of enzyme (9310 IGIU) was pumped into the column. The column was then washed with 50 ml of water to remove residual isomerase and then with 50 ml of salt elution solution (0.6 M NaCl, 0.2 mM $CoCl_2$) to remove adsorbed impurities. The wash water and salt-elute were assayed for isomerase activity.

The effluent from the column and the wash water contained a total of 8890 IGIU, indicating that all but about 420 IGIU had been desorbed from the DEAE-cellulose bed. The salt eluate contained 386 IGIU, leaving only 34 IGIU unaccounted for and a total activity accountability of greater than 99%.

By extrapolation of the experimental results (FIG. 2), it's predicted that a total of 1012 ml of extract (46 fractions) or about 9900 IGIU could be applied to the 1 g bed of DEAE-cellulose before isomerase was completely displaced by the more strongly bound components of the crude extract. Thus, a 1 g bed of DEAE-cellulose is sufficient to refine almost 10,000 IGIU of crude isomerase extract. Surprisingly, the equilibria among isomerase, substances which compete with isomerase for adsorption on DEAE-cellulose, and the DEAE-cellulose is established very rapidly at room temperature since the contact time (residence time) was only about 10 minutes. Apparently, substances in the untreated enzyme extract which are strongly adsorbed by DEAE-cellulose can displace or desorb adsorbed isomerase quite readily and almost quantitatively while these substances are themselves retained on the DEAE-cellulose bed. Thus, no added material is necessary to elute the enzyme from the column. In addition, the concentration of isomerase in the eluate (~16 IGIU/ml) is greater than the enzyme concentration in the extract applied to the column.

EXAMPLE II

This example compares the ability of DEAE-cellulose to adsorb the treated and untreated isomerase of Example I. The adsorption isotherms were determined at room temperature and pH 6.8.

Fractions number 21 thru 40 of Example I were combined and diluted with deionized water to a total volume of 500 ml, containing a total of 6100 IGIU. DEAE-cellulose was added in 200 mg (d.b.) increments. After each addition, the suspension was stirred for 30 minutes, an aliquot was taken, filtered, and the filtrate assayed for isomerase activity. Additions were continued until the soluble activity assay indicated that all the activity had been adsorbed. The results are reported in Table II.

TABLE II
TREATED ISOMERASE ACTIVITY ADSORBED ON DEAE-CELLULOSE

| Total DEAE-Cellulose Added (mg, d.b.) | Soluble Activity IGIU/ml | Total IGIU | Adsorbed Activity IGIU-by Difference[1] |
|---|---|---|---|
| 0 | 12.2 | 6100 | 0 |
| 200 | 10.0 | 5000 | 1100 |
| 400 | 7.0 | 3500 | 2600 |
| 600 | 4.6 | 2300 | 3800 |
| 800 | 2.0 | 1000 | 5100 |
| 1000 | 0.2 | 100 | 6000 |
| 1200 | 0 | 0 | 6100 |

[1] These data are depicted in FIG. 3.

In a like manner, DEAE-cellulose was added to 500 ml of the untreated isomerase, containing a total of 4900 IGIU, and the soluble activity after each addition determined. The results are reported in Table III.

TABLE III
UNTREATED ISOMERASE ACTIVITY ADSORBED ON DEAE-CELLULOSE

| Total DEAE-Cellulose Added (mg, d.b.) | Soluble Activity IGIU/ml | Total IGIU | Adsorbed Activity IGIU-by Difference |
|---|---|---|---|
| 0 | 9.8 | 4900 | 0 |
| 200 | 9.0 | 4500 | 400 |
| 400 | 8.0 | 4000 | 900 |
| 600 | 7.4 | 3700 | 1200 |
| 800 | 4.0 | 2000 | 2900 |
| 1000 | 1.8 | 900 | 4000 |
| 1500 | 0.2 | 100 | 4800 |

[1] These data are depicted in FIG. 3.

A comparison of the DEAE-cellulose adsorptivity of the treated and untreated isomerase is shown in FIG. 3. This figure illustrates that 1 g (100 mg) of DEAE-cellulose adsorbed 6000 IGIU of the treated isomerase compared to only 4000 IGIU of the untreated isomerase. Thus, the treatment of glucose isomerase by the process of the invention resulted in a marked increase (50%) in the adsorption of the isomerase by DEAE-cellulose.

EXAMPLE III

This example illustrates further the usefulness of the fixed-bed refining technique by showing that the fixed-bed can be easily regenerated in situ and reused.

Crude isomerase extract, 11.0 IGIU/ml, (prepared as described in Example I) was passed through a 1.0 g bed of DEAE-cellulose (1.5×10.2 cm) at a flow rate of about 1.0 ml/min. The effluent from this column was collected in 22-ml fractions each of which was assayed for isomerase. A total of 3400 IGIU was applied to the column before enzyme began to appear in the effluent at a peak activity of about 20 IGIU/ml, almost double that of the crude extract applied to the column. After 50 fractions had been collected (12,232 IGIU applied to the column) the effluent activity was 11.2 IGIU/ml, virtually the same as the crude extract applied to the column, indicating that the DEAE-cellulose was saturated with strongly bound material and that no isomerase was being adsorbed or desorbed. The column was then washed 50 ml of water to remove entrained extract and was then eluted with 50 ml of salt solution to remove adsorbed materials. A total of only 63.5 IGIU was found in the salt eluate. Total recovery of activity in the column effluent and water wash was 12,143 IGIU or better than 99% of the activity applied to the column.

Adsorption isotherms were run with portions of the column effluent using DEAE-cellulose as the adsorbent at pH 6.8, room temperature. The adsorption was greater than 5900 IGIU per gram of DEAE-cellulose. Thus, the column refining procedure again resulted in a marked increase in isomerase adsorption.

The DEAE-cellulose bed from the above refining operation was washed in situ with 1000 ml of water at a flow rate of about 3 ml/min. to remove residual salt. The washed DEAE-cellulose bed was then reused to refine more crude extract as described below.

A fresh crude isomerase extract, 9.25 IGIU/ml, was prepared and passed through the washed DEAE-cellulose bed under conditions identical to those described above. The regenerated DEAE-cellulose bed performed almost as well as the fresh DEAE-cellulose. The capacity of the DEAE-cellulose bed for isomerase was reduced only slightly from about 3400 IGIU for the first use to about 3300 IGIU after regeneration. A total of 9360 IGIU was applied to the column in the second use and 9220 IGIU was recovered in the effluent plus an additional 160 IGIU in the salt eluate. These results showed that the DEAE-cellulose bed can be easily regenerated in situ by salt elution to remove adsorbed materials and water washing to remove residual salt.

What is claimed is:

1. A chromatographic process for producing a purified enzyme preparation comprising contacting an impure liquid enzyme preparation containing enzyme and soluble impurities with an ion exchange material known to adsorb the enzyme in a column wherein both the enzyme and the soluble impurities are adsorbed by the ion exchange material and adding an additional amount of the impure liquid enzyme preparation whereby the soluble impurities in the additional impure liquid enzyme preparation are preferentially adsorbed by the ion exchange material and the adsorbed enzyme is displaced from the ion exchange material thereby producing a purified liquid enzyme preparation substantially more concentrated than the impure liquid enzyme preparation.

2. The process of claim 1, wherein the ion exchange material is an anion exchange cellulose or a synthetic macroporous anion exchange resin.

3. The process of claim 2, wherein the enzyme in the impure liquid enzyme preparation is selected from the group consisting of glucose isomerase, alpha amylase, and glucoamylase.

4. The process of claim 3, wherein the anion exchange cellulose is DEAE-cellulose and the enzyme in the aqueous enzyme preparation is glucose isomerase.

5. A process for producing an immobilized enzyme preparation comprising contacting an impure liquid enzyme preparation containing enzyme and soluble impurities with a first ion exchange material known to adsorb the enzyme in a column chromatographic process wherein both the enzyme and the soluble impurities are adsorbed by the first ion exchange material and adding an additional amount of the impure liquid enzyme preparation whereby the soluble impurities in the additional impure liquid enzyme preparation are preferentially adsorbed by the first ion exchange material and the adsorbed enzyme is displaced from the first ion exchange material thereby producing a purified liquid enzyme preparation substantially more concentrated than the impure liquid enzyme preparation, and contacting the purified liquid enzyme preparation with a second ion exchange material to adsorb the enzyme and produce a high activity immobilized enzyme preparation.

6. The process of claim 5, wherein the second ion exchange material is anion exchange cellulose or a synthetic macroporous anion exchange resin.

7. The process of claim 6, wherein the first ion exchange material is anion exchange cellulose or a synthetic macroporous anion exchange resin.

8. The process of claim 7, wherein the impure liquid enzyme preparation is an aqueous solution.

9. The process of claim 9, wherein the enzyme in the aqueous enzyme preparation is selected from the group consisting of glucose isomerase, alpha amylase, and glucoamylase.

10. The process of claim 9, wherein the second ion exchange material is DEAE-cellulose.

11. The process of claim 10, wherein the enzyme in the aqueous enzyme preparation is glucose isomerase.

* * * * *

UNITED STATES PATENT OFFICE
CERTIFICATE OF CORRECTION

PATENT NO. : 4,347,322
DATED : August 31, 1982
INVENTOR(S) : Richard A. Johnson, et al.

It is certified that error appears in the above-identified patent and that said Letters Patent are hereby corrected as shown below:

Column 2, line 24, "of" should read -- on --;

line 47, "te" should read -- the --;

Column 3, line 9, "for" should read -- from --;

Column 4, line 7, "describes" should read -- describe --;

Column 8, line 18, heading of Table I, "Inffluent" should read -- Influent --;

Column 9, line 67, "(100 mg)" should read -- (1000 mg) --;

Column 12, line 17, "9" should read -- 8 --.

Signed and Sealed this

Seventh Day of December 1982

[SEAL]

Attest:

GERALD J. MOSSINGHOFF

Attesting Officer    Commissioner of Patents and Trademarks